United States Patent
Hitz et al.

(10) Patent No.: US 9,839,719 B2
(45) Date of Patent: Dec. 12, 2017

(54) BIOCOMPATIBLE POLYMERS AND CO-POLYMERS, AND USES THEREOF

(75) Inventors: Hans Hitz, Arisdorf (CH); Rolf Schäfer, Arisdorf (CH); Christoph Schäfer, Bubendorf (CH)

(73) Assignee: CIS PHARMA AG, Bubendorf (CH)

( * ) Notice: Subject to any disclaimer, the term of this patent is extended or adjusted under 35 U.S.C. 154(b) by 610 days.

(21) Appl. No.: 11/920,507

(22) PCT Filed: May 22, 2006

(86) PCT No.: PCT/IB2006/001722
§ 371 (c)(1),
(2), (4) Date: Nov. 16, 2007

(87) PCT Pub. No.: WO2006/126095
PCT Pub. Date: Nov. 30, 2006

(65) Prior Publication Data
US 2009/0232871 A1    Sep. 17, 2009

Related U.S. Application Data

(60) Provisional application No. 60/684,175, filed on May 25, 2005.

(51) Int. Cl.
*A61L 29/00* (2006.01)
*A61L 27/16* (2006.01)

(52) U.S. Cl.
CPC .................................... *A61L 27/16* (2013.01)

(58) Field of Classification Search
None
See application file for complete search history.

(56) References Cited

U.S. PATENT DOCUMENTS

| | | | |
|---|---|---|---|
| 4,663,409 A | 5/1987 | Friends et al. | |
| 5,693,095 A | 12/1997 | Freeman et al. | |
| 6,703,468 B1 * | 3/2004 | Otiai et al. | 526/307.6 |
| 6,767,979 B1 * | 7/2004 | Muir et al. | 526/262 |
| 2002/0180927 A1 | 12/2002 | Polzhofer et al. | |
| 2003/0175324 A1 * | 9/2003 | Robinson et al. | 424/427 |
| 2014/0065226 A1 | 3/2014 | Brey et al. | |

FOREIGN PATENT DOCUMENTS

| | | | | |
|---|---|---|---|---|
| EP | 0443809 | * | 2/1991 | A61F 2/16 |
| EP | 0443809 | | 8/1991 | |
| EP | 0485197 | * | 11/1991 | C08F 220/30 |
| EP | 0485197 | | 5/1992 | |
| EP | 1156031 A1 | | 11/2001 | |
| JP | 10-298238 A | | 11/1998 | |
| JP | 2001026573 A | | 1/2001 | |

OTHER PUBLICATIONS

Database WPI Week 200141. Derwent Publications Ltd., Londo, GB; AN 2001-384367, XP002437011, 2001.
Hayden CGJ et al. Sunscreen penetration of human skin . . . Skin Pharmacology and Physiology 18: 170-4 (2005) ISSN 1660-5527.
Jiang B et al. Invest. of lysine acrylate containing poly(N-isopropylacrylamide) hydrogels . . . J Biomed Mater Res Part B 100: 668-76 (2012).

* cited by examiner

*Primary Examiner* — Brian Gulledge
(74) *Attorney, Agent, or Firm* — Richard Voellny

(57) ABSTRACT

The invention relates to highly biocompatible or biophilic un-cross-linked or cross-linked polymers comprising one or more side-chain active acrylic amino acids of formula I

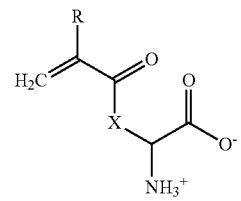

wherein: X is $-NH(CH_2)_4-$, $-O-C_6H_4-CH_2-$, $-OCH_2-$, $-O-CH(CH_3)-$, $-S-CH_2-$, $-O$-proline, and R is H or $CH_3$; and wherein the polymer further includes a free radical initiator and, optionally, a cross-linking agent having a plurality of polymerizable ethylenically unsaturated groups. The invention further concerns various highly biocompatible, cross-linked co-polymers comprising one or more monomers of formula I, and one or more other polymerizable monomers. Uses of such polymers and co-polymers for the production of contact lenses, intraocular lenses, implants, wound healing slabs, additives for food and cosmetics, conductive plastics, spinnable fibers, and the like are disclosed.

12 Claims, No Drawings

BIOCOMPATIBLE POLYMERS AND CO-POLYMERS, AND USES THEREOF

FIELD OF THE INVENTION

This application relates to new biocompatible polymers and co-polymers comprising side chain-active amino acids, as well as to uses of these polymers, for medical devices, implants, additives for food and cosmetics, fibers for fabrics and in particular for the preparation of optical lenses.

BACKGROUND OF THE INVENTION

Synthetic polymers are widely used in biomedical applications as well as in other articles that come into contact with human skin or tissues, including clothing. Polymers frequently used in biomedical applications include acrylics, polyurethanes, silicones and various hydrophilics. In the area of optical lenses, including intraocular and contact lenses, typically used polymers are polymethylmethacrylate, polyphenylethyl methacrylate, cellulose acetate butyrate, silicone-methylmethacrylate co-polymers, methylmethacrylate co-polymers with hydrophilic compounds, as well as hydrogels such as those based on hydroxyethylmethacrylate and dihydroxypropylmethacrylate. Common to these materials is that they provide for surfaces that are very different from known biological surfaces and therefore exhibit various degrees of tissue- or bio-incompatibility. Co-polymers that include amino acids were described by Bawa in U.S. Pat. No. 4,668,506. However, because the amino acids contained in the polymers described by Bawa are anionic and lack free alpha-amino-carbonic acid groups, they do not significantly improve the biocompatibility of polymers. The present invention specifically relates to polymers and co-polymers of side chain-active acrylic amino acids. Side chain active acrylic amino acids are not miscible with acrylic building blocks in solvent-free systems of the state of the art. It was surprisingly found that protective groups added to the α-amino group of the building blocks of the invention made the side chain-active acrylic amino acids miscible with acrylic building blocks of the state of the art. The inclusion of amino acids or amino acid derivatives containing free alpha-amino-carbonic acid groups (after deprotection of the α-amino-group) in the polymers or co-polymers of the invention results in polymer surfaces that exhibit tissue compatibilities or bio-compatibilities that closely resemble those of biological materials. Because the amino acids or amino acid derivatives incorporated in the polymers are not linked via peptidic bonds, the polymers are resistant to biological degradation by tissue proteases. Furthermore, the presence of amino acids or amino acid derivatives in the polymers of the invention increases their hydrophilicity. This property translates into enhanced uptake of water, oxygen permeability and surface wetting.

SUMMARY OF THE INVENTION

The present invention relates to highly biocompatible polymers comprising one or more polymerizable monomers of formula I

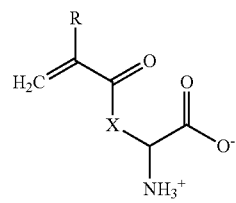

wherein: X is —NH(CH$_2$)$_4$—, —O—C$_6$H$_4$—CH$_2$—, —OCH$_2$—, —O—CH(CH$_3$)—, —S—CH$_2$—, —O-proline, and R is H or CH$_3$; and wherein the polymers further include a thermal or photosensitive free radical initiator and, optionally, a cross-linking agent having a plurality of polymerizable ethylenically unsaturated groups. Polymers of this type are particularly useful for the production of breast implants, space fillers for surgery, slabs for the treatment of skin burns, ointments of any kind, food and cosmetic additives and the like.

The invention further concerns highly biocompatible co-polymers comprising one or more polymerizable principal monomers, which monomers are characterized as having at least one ethylenically unsaturated group, and one or more monomers of formula I. The co-polymers further include a free radical initiator and, optionally, a cross-linking agent having a plurality of polymerizable ethylenically unsaturated groups. The co-polymers may also include a photosensitizer, an ultraviolet-absorbing compound and a blue light-absorbing compound.

Co-polymers of this type are particularly useful for the production of medical devices, implants, additives for food and cosmetics, conductive plastics and fibers for fabrics. Hydrogel co-polymers of the invention may be prepared by co-polymerization of at least one principal monomeric component which will have a hydrophilic nature and be capable of forming a hydrogel in a cross-linked polymer and one or more monomers of formula I.

In a particular embodiment of the co-polymers of the invention, the polymerizable principal monomers are combinations of two monomers capable of forming a hydrogel. Suitable combinations of principal monomers include hydroxyethylmethacrylate and methyl methacrylate, vinyl pyrrolidone and hydroxyethylmethacrylate, vinyl pyrrolidone and methyl methacrylate, glyceral methacrylate and methyl methacrylate, glyceryl-methacrylate and 2-hydroxyethylmethacrylate, hydroxyethylmethacrylate or diacetone acyl amide and hydroxyalkyl methacrylates, hydroxyethylmethacrylate or diacetone acyl amide and acrylates with the alkyl groups having from 2 to 6 carbon atoms, hydroxyethylmethacrylate or diacetone acyl amide and vinyl hydroxy acetate, hydroxyethylmethacrylate or diacetone acyl amide and vinyl hydroxy propionate, hydroxyethylmethacrylate or diacetone acyl amide and vinyl hydroxy butyrate, hydroxyethylmethacrylate or diacetone acyl amide and N-vinyl lactams namely N-vinyl pyrrolidone, N-vinyl caprolactam and N-vinyl piperidone, hydroxyethylmethacrylate or diacetone acyl amide and N,N dialkyl amino ethyl methacrylates and acrylates with the alkyl groups having from 0 to 2 carbon atoms, hydroxyethylmethacrylate or diacetone acyl amide and hydroxyalkyl vinyl ethers with the alkyl groups having 2 to 4 carbon atoms, hydroxyethylmethacrylate or diacetone acyl amide and 1-vinyloxy 2-hydroxyethylene, hydroxyethylmethacrylate or diacetone acyl amide and 1-vinyloxy 5-hydroxy 3-oxapentane, hydroxyethylmethacrylate or diacetone acyl amide and 1-vinyloxy 8-hydroxy 3,6-dioxaoctane, hydroxyethylmethacrylate or diacetone acyl amide and 1-vinyloxy 14-hydroxy 3,6,9,12 tetraoxatetradectane, hydroxyethylmethacrylate or diacetone acyl amide and N-vinyl morpholine; hydroxyethylmethacrylate or diacetone acyl amide and N,N dialkyl acrylamide with the alkyl groups having from 0 to 2 carbons atoms, hydroxyethylmethacrylate or diacetone acyl amide and alkyl vinyl ketone with the alkyl group having 1 to 2 carbon atoms, hydroxyethylmethacrylate or diacetone acyl amide and N-vinyl succinimide or N-vinyl glutarimide, hydroxyethylmethacrylate or diacetone acyl amide and N-vinyl imidazole, and hydroxyethylmethacrylate or diacetone acyl amide and N-vinyl 3-morpholinone. In addition to one or more co-principal monomers according to formula I, the co-polymers further include a free radical initiator and, optionally, a cross-linking agent having a plurality of polymerizable ethylenically unsaturated groups. The co-polymers may additionally include a photosensitizer, an ultraviolet-absorbing compound and a blue light-absorbing compound. The co-polymers are suitable for the production of hydrogel contact lenses. They can also be used to produce single-piece and bicomposite intraocular lenses. In the case of bicomposite ocular lenses that consist of an optic portion and a haptic portion, optic portion and haptic portion may be produced from similar co-polymers, provided that the co-polymer used for the manufacture of the haptic portion has a lower water content in its hydrated form than the co-polymer from which the optic portion is made. The term "similar co-polymers" means that co-polymers are made from identical monomers or from equivalent combinations of monomers such as those listed above, with the proviso that the relative amounts of monomers can vary to produce co-polymers of differing water contents.

In a particular embodiment, a co-polymer of the invention comprises one or more principal monomers according to formula III

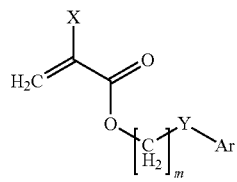

wherein: X is H or $CH_3$; m is 0-10; Y is nothing, O, S, or NR wherein R is H, $CH_3$, $C_nH_{2n+1}$ (n=1-10) iso-$OC_3H_7$, $C_6H_5$, or $CH_2C_6H_5$; Ar is any aromatic ring, such as benzene, which can be unsubstituted or substituted with H, $CH_3$, $C_2H_5$, n-$C_3H_7$, iso-$C_3H_7$, $OCH_3$, $C_6H_{11}$, Cl, Br, $C_6H_5$ or $CH_2C_6H_5$. In addition to one or more co-principal monomers according to formula I, the co-polymers further include a free radical Initiator and, optionally, a cross-linking agent having a plurality of polymerizable ethylenically unsaturated groups. The co-polymers may also include a photosensitizer, an ultraviolet-absorbing compound and a blue light-absorbing compound. Suitable monomers according to formula III include 2-ethylphenoxy acrylate, 2-ethylphenoxy methacrylate, 2-ethylthiophenyl acrylate, 2-ethylthiophenyl methacrylate, 2-ethylaminophenyl acrylate, 2-ethylaminophenyl methacrylate, phenyl acrylate, phenyl methacrylate, benzyl acrylate, benzyl methacrylate, 2-phenylethyl acrylate, 2-phenylethyl methacrylate, 3-phenylpropyl acrylate, 3-phenylpropyl methacrylate, 3-propylphenoxy acrylate, 3-propylphenoxy methacrylate, 4-butylphenoxy acrylate, 4-butylphenoxy methacrylate, 4-phenylbutyl acrylate, 4-phenylbutyl methacrylate, 4-methylphenyl acrylate, 4-methylphenyl methacrylate, 4-methylbenzyl acrylate, 4-methylbenzyl methacrylate, 2-2-methylphenylethyl acrylate, 2-2-methylphenylethyl methacrylate, 2-3-methylphenylethyl acrylate, 2-3-methylphenylethyl methacrylate, 2-4-methylphenylethyl acrylate, 2-4-methylphenylethyl methacrylate, 2-(4-propylphenyl)ethyl acrylate, 2-(4-propylphenyl)ethyl methacrylate, 2-(4-(1-methylethyl)phenyl)ethyl acrylate, 2-(4-(1-methylethyl)phenyl)ethyl methacrylate, 2-(4-methoxyphenyl)ethyl acrylate, 2-(4-methoxyphenyl)ethyl methacrylate, 2-(4-cyclohexylphenyl)ethyl acrylate, 2-(4-cyclohexylphenyl)ethyl methacrylate, 2-(2-chlorophenyl)ethyl acrylate, 2-(2-chlorophenyl)ethyl methacrylate, 2-(3-chlorophenyl)ethyl acrylate, 2-(3-chlorophenyl)ethyl methacrylate, 2-(4-chlorophenyl)ethyl acrylate, 2-(4-chlorophenyl)ethyl methacrylate, 2-(4-bromophenyl)ethyl acrylate, 2-(4-bromophenyl)ethyl methacrylate, 2-(3-phenyl-phenyl)ethyl acrylate, 2-(3-phenylphenyl)ethyl methacrylate. 2-(4-phenylphenyl)ethyl methacrylate, 2-(4-phenylphenyl)ethyl methacrylate, 2-(4-benzylphenyl)ethyl acrylate, and 2-(4-benzylphenyl)ethyl methacrylate. 2-Phenylethyl acrylate and 2-phenylethyl methacrylate represent a preferred combination of monomers according to formula III. Co-polymers comprising one or more monomers of formula III and one or more monomers of formula I are suitable for the production of highly biocompatible, foldable intraocular lenses.

In another particular embodiment, a co-polymer of the invention comprises two principal polymerizable monomers, the first being a monomer whose homopolymers have a refractive index of at least 1.50 and the second being a monomer whose homopolymers have a glass transition temperature of less than 30° C., preferably less than 22° C. In addition to one or more co-principal monomers according to formula I, the co-polymers further include a free radical initiator and, optionally, a cross-linking agent having a plurality of polymerizable ethylenically unsaturated groups. The co-polymers may additionally include a photosensitizer, an ultraviolet-absorbing compound and a blue light-absorbing compound. Suitable first principal monomers include styrene, vinyl carbazole, vinyl naphthalene, benzyl acrylate, phenyl acrylate, naphthyl acrylate, pentabromophenyl acrylate, 2-phenoxyethyl acrylate, 2-phenoxyethyl methacrylate, and 2,3-dibromopropyl acrylate. Suitable second principal monomers comprise n-butyl acrylate, n-hexyl acrylate, 2-ethylhexyl acrylate, 2-ethoxyethyl acrylate, 2,3-dibromopropyl acrylate, n-1, and 1-dihydroperfluorobutyl acrylate. The co-polymers may, optionally, further comprise a hydrophilic principal monomer. Choice hydrophilic monomers include N-vinyl pyrrolidone, a hydroxyalkyl acrylate or methacrylate such as 2-hydroxyethyl acrylate, 2-hydroxyethyl methacrylate, 3-hydroxypropyl acrylate, 3-hydroxypropyl methacrylate, 4-hydroxybutyl acrylate, 4-hydroxybutyl methacrylate, 2,3-dihydroxypropyl acrylate, or 2,3-dihydroxypropyl methacrylate, acrylamide, an N-alkyl acrylamide such as N-methyl acrylamide, N-ethyl acrylamide, N-propyl acrylamide, or N-butyl acrylamide; acrylic acid; and methacrylic acid. The latter co-polymers are suitable for the production of highly biocompatible, soft contact lenses or soft, foldable intraocular lenses or optic portions thereof having a high refractive index.

In a further particular embodiment, a co-polymer of the invention comprises as principal polymerizable monomers a monomer of formula III and a hydrophilic monomer. A suitable hydrophilic monomer is selected from the group consisting of 2-hydroxyethyl acrylate, 2-hydroxyethyl methacrylate, 2-N-ethylacrylate pyrrolidone, 2-hydroxy-3-phenoxypropyl acrylate, 2,3-dihydroxypropyl acrylate, 2,3-dihydroxypropyl methacrylate, 2-N-vinyl pyrrolidone, polyethylene oxide:200 monomethyl ether monomethacrylate, polyethylene oxide:200 monomethacrylate, and polyethylene oxide:1000 dimethacrylate. In addition to one or more co-principal monomers according to formula I, the co-polymers further include a free radical initiator and, optionally, a cross-linking agent having a plurality of polymerizable ethylenically unsaturated groups. The co-polymers may additionally include a photosensitizer, an ultraviolet-absorbing compound and a blue light-absorbing compound. The latter co-polymers are suitable for the production of highly biocompatible, soft contact lenses or soft, foldable intraocular lenses or optic portions thereof having a high refractive index.

In a different embodiment, the polymers and co-polymers of the invention are used to produce drug delivery devices for topical, systemic and transdermal administration of a drug. These drug delivery devices comprise a polymer or co-polymer of the invention and a drug in a therapeutically effective amount. A therapeutically effective amount of a drug is an amount that produces a desired therapeutic effect for the intended period of time. The co-polymers of the invention can also be used to manufacture contact lenses or intraocular lenses containing a therapeutically effective amount of a drug. Such medicated lenses are capable of delivering the drug to ocular tissue or to the circulation.

DETAILED DESCRIPTION

The present invention relates to polymers and co-polymers comprising one or more monomers consisting of side-chain active acrylic amino acids. The side-chain active acrylic amino acids used in the polymers and co-polymers of the invention are acryl or methacryl derivatives of lysine, tyrosine, serine, threonine, cysteine, or hydroxyproline. The structure of the side chain-active acrylic amino acids of interest in the invention is represented in formula I:

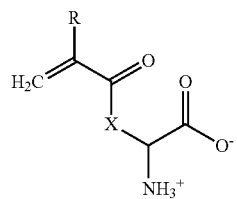

wherein: X is —NH(CH$_2$)$_4$—, —O—C$_6$H$_4$—CH$_2$—, —OCH$_2$—, —O—CH(CH$_3$)—, —S—CH$_2$—, —O-proline; and R is H or CH$_3$.

The synthesis of side chain-active acrylic amino acids was described previously. Zbaida et al. 1987. Reactive Polymers 6, 241-253. They can be prepared by reacting the amino acid copper complex of lysine, tyrosine, serine, threonine, cysteine or hydroxyproline with acryl or methacryl chloride, followed by treatment with a stream of hydrogen sulfide or sodium sulfide in acidic solution to yield the unprotected monomer. Alternatively, alpha-amino-protected amino acid (e.g., Fmoc amino acid) is reacted directly with acryl or methacryl chloride. The protective group is then removed in a subsequent step, subsequent to formation of homo- or co-polymers. The two types of synthesis methods are described in detail in the example section.

Polymers of side chain-active acrylic amino acids, of formula I can be prepared using conventional polymerization methods. Side chain-active acrylic amino acids are dissolved in an appropriate polar solvent (e.g., water or a mixture of water and dimethyl formamide) together with a conventional free-radical initiator. The mixture can then be poured into a suitable container or mold, wherein polymerization is induced. Initiators can be thermal initiators or photoinitiaters. Typical thermal free radical initiators include peroxides, such as benzophenone peroxide, peroxycarbonates such as bis-(4-t-butylcyclohexyl) peroxydicarbonate, azonitriles such as azobisisobuytyronitrile, and the like. A preferred initiator is bis-(4-t-butylcyclohexyl) peroxydicarbonate. Alternatively, the monomers can be photopolymerized in a container or mold that is transparent to radiation of a wavelength capable of initiating polymerization of the acrylic monomers. Conventional photoinitiator compounds, e.g., a benzophenone-type photoinitiator, can also be introduced to facilitate the polymerization. Photosensitizers can be introduced as well to permit the use of longer wavelengths; however, when preparing a polymer which is intended for long residence within or in contact with the human body or a human tissue, it is generally preferable to keep the number of ingredients in the polymer to a minimum to avoid the presence of materials which might leach out from the polymer into the tissue. Co-polymers of the invention comprising one or more types of monomers of formula I and one or more other reactive monomers are prepared in the absence of any solvent using alpha-amino-protected side chain-active amino acids. A preferred protective group is Fmoc. This protective group can be removed subsequent to polymerization by deprotection in dimethylformamide and piperidine (8:1).

Polymerization mixtures for the production of polymers and co-polymers of the invention typically also include a co-polymerizable cross-linker. A suitable cross-linking agent may be any terminally ethylenically unsaturated compound having more than one unsaturated group, i.e., a multiplicity of unsaturated groups. More particularly, suitable cross-linking agents include, but are not limited to, the following: ethylene glycol diacrylate or dimethacrylate, diethylene glycol diacrylate or dimethacrylate, triethylene glycol diacrylate or dimethacrylate, tetraethylene glycol diacrylate or dimethacrylate, polyethylene glycol diacrylate or dimethacrylate, trimethylolpropane triacrylate or trimethacrylate, bisphenol A diacrylate or dimethacrylate, ethoxylated bisphenol A diacrylate or dimethacrylate, pentaerythritol tri- and tetra-acrylate or methacrylate, tetramethylene diacrylate or dimethacrylate, methylene bisacrylamide or methacrylamide, dimethylene bisacrylamide or methacrylamide, N,N'-dihydroxyethylene bisacrylamide or methacrylamide, hexamethylene bisacrylamide or methacrylamide, decamethylene bisacrylamide or methacrylamide, divinyl benzene, vinyl methacrylate, allyl methacrylate, etc. Additional useful cross-linking agents include 1,3-bis(4-methacryloyl oxyalkyl)tetra disiloxane and similar poly(organosiloxane) monomers set forth in U.S. Pat. No. 4,153,641. Another group of useful cross-linking agents are the resonance-free di(alkylene tertiary amine) cyclic compounds, e.g., N,N'-divinyl ethylene urea, as disclosed in U.S. Pat. No. 4,436,887. Yet another group are di- or polyvinyl ethers of di- or polyvalent alcohols such as ethylene glycol divinyl ether. Cross-linking agents can be used in varying amounts from about 0.1 wt % to about 20 wt %, but are preferably present in an amount of about 0.5 wt % of total monomers present.

Fmoc-protected side chain-active acrylic amino acids of formula I can be co-polymerized with one or more other reactive monomers. Hydrophilic reactive monomers include, for example, the hydroxyalkyl esters and amides, both N-substituted and unsubstituted, of alpha-, beta-unsaturated carboxylic acids, N-vinyl lactams and 2-acrylamido-2-methylpropane sulfonic acid. The alpha-, beta-unsaturated acids useful in this invention are acrylic acid, crotonic acid, methacrylic acid, itaconic acid, maleic acid, maleic anhydride, fumaric acid and the like. The poly-functional alcohols which form the hydroxyalkyl esters include glycol, glycerol, propylene glycol, trimethylene glycol and other polyhydric alkanols, dialkylene glycols of 2 to 12 carbon atoms, polyalkylene glycols, etc. Polyalkylene glycols are exemplified by triethylene glycol, tetraethylene glycol, pentaethylene glycol, hexaethylene glycol and the like. The preferred hydrophilic monomers are the hydroxyalkyl esters, specifically hydroxyethyl methacrylate. Suitable hydrophobic monomers include cycloalkyl ester, tertiary-butyl styrene, polycyclic acrylate or methacrylate, and the like as well as mixtures thereof. More particularly, the polycyclic acrylics may be isobornyl acrylate, isobornyl methacrylate, dicyclopentanedienyl acrylate, dicyclopentanedienyl methacrylate, adamantyl acrylate, adamantyl methacrylate, isopinocamphyl acrylate, isopinocamphyl methacrylate, etc., and mixtures thereof. Cycloalkyl ester monomer is of formula II below (Formula I from U.S. Pat. No. 506). Illustrative of these cycloalkyl esters are menthyl methacrylate, menthyl acrylate, tertiary-butyl cyclohexyl methacrylate, isohexyl cyclopentyl acrylate, methylisopentyl cyclooctyl acrylate and the like.

Formula I from U.S. Pat. No. 506

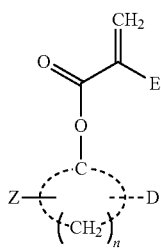

wherein: D is branched or normal alkyl of 3 to 6 carbon atoms, E is H or $CH_3$, Z is H or $CH_3$, and n is an integer from 3 to 8.

Other well known hydrophobic monomers may be used in the formulation of the co-polymers of the invention, including monomers containing at least one silicon or fluorine atom as a part of their composition. Hydrophobic monomers include alkyl, cyclo-alkyl and aryl acrylates and methacrylates as well as mono- or disubstituted itaconates, styrene and its derivatives, acrylonitrile, vinyl esters such as vinyl acetate or vinyl pentacetyl gluconate, vinyl ethers such as vinyl butyl ether, allyl esters such as allyl acetate, propionate or butyrate, fluorine containing monomers such as octafluoropentyl methacrylate and silicon containing monomer, e.g., 1,1,1-tris(trimethoxysiloxy)-3-methacryloxy propylsilane or heptamethyltrisiloxanyl ethyl acrylate. Typically, a side chain-active acrylic amino acid of formula I and other reactive monomers will be present in the co-polymers of the invention at weight ratios between 1:99 and 1:1, more preferably between about 1:9 and 1:4.

Hydrogel co-polymers of the invention may be prepared by co-polymerization of one or more monomers of formula I and one or more other monomeric components, at least one of which will have a hydrophilic nature and be capable of forming a hydrogel in a cross-linked polymer. "Hydrogels" are understood to be cross-linked polymers that, upon hydration, have an equilibrium content of between about 5% and 95% percent water. Hydrogel co-polymers of the invention can be used for the manufacture of biocompatible, soft optical lenses, including contract lenses and foldable intraocular lenses (IOL). The optic portion of a foldable IOL or a soft contact lens will preferably have a water content of at least about 25%.

Suitable combinations of monomeric components that may be co-polymerized in the presence of one or more monomers of formula I to produce hydrogel co-polymers of the invention that are suitable for the preparation of biocompatible hydrogel optical lenses comprise hydroxyethylmethacrylate and methyl methacrylate, vinyl pyrrolidone and hydroxyethylmethacrylate or methyl methacrylate; glyceral methacrylate and methyl methacrylate; hydroxyethylmethacrylate/diacetone acyl amide and hydroxyalkyl methacrylates, acrylates with the alkyl groups having from 2 to 6 carbon atoms; vinyl hydroxy acetate, vinyl hydroxy propionate, vinyl hydroxy butyrate; N-vinyl lactams namely N-vinyl pyrrolidone, N-vinyl caprolactam and N-vinyl piperidone; N,N dialkyl amino ethyl methacrylates and acrylates with the alkyl groups having from 0 to 2 carbon atoms; hydroxyalkyl vinyl ethers with the alkyl groups having 2 to 4 carbon atoms; 1-vinyloxy 2-hydroxyethylene, 1-vinyloxy 5-hydroxy 3-oxapentane, 1-vinyloxy 8-hydroxy 3,6-dioxaoctane, 1-vinyloxy 14-hydroxy 3,6,9,12 tetraoxatetradecane; N-vinyl morpholine; N,N dialkyl acrylamide with the alkyl groups having from 0 to 2 carbons atoms; alkyl vinyl ketone with the alkyl group having 1 to 2 carbon atoms; N-vinyl succinimide and N-vinyl glutarimide; N-vinyl imidazole; and N-vinyl 3-morpholinone.

The co-polymers of one or more monomers of formula I and one or more other suitable reactive monomers are prepared generally by conventional polymerization methods. A mixture of the liquid monomers in the desired proportions together with a suitable cross-linking agent and a conventional free-radical initiator is prepared. The mixture can then be introduced into a mold of suitable shape to produce an article of interest such as a lens, or optical lens and haptic as the case may be. Typical thermal free radical initiators and photoinitiator compounds as well as photosensitizers were described before. Polymerization can then be initiated by heating or irradiation, respectively.

Concerning foldable IOLs prepared from co-polymers of the invention, these lenses can be of any design capable of being rolled or folded into a small cross section that can fit through a relatively small incision. For example, the IOLs can be of what is known as a one-piece or multipiece design. Typically, an IOL comprises an optic and at least one haptic. The optic is that portion which serves as the lens, and the haptics are attached to the optic and are like arms that hold the optic in its proper place in the eye. The optic and haptic(s) can be of the same or different material. A multipiece lens is so called because the optic and the haptic(s) are made separately, and then the haptics and the optic are joined. In a one-piece lens, the optic and the haptic(s) are formed out of one piece of material. Depending on the material, the haptic(s) is then cut, or lathed, out of the material to produce the IOL. Particularly in the case of hydrogel IOLs, multipiece lenses may be preferred. A haptic portion can be used that has a low water content (as low as 5%). This low water hydrogel can be any co-polymer of the invention which will allow for a self supporting IOL, i.e., the haptics are rigid enough to allow for construction of narrow diameter loop type haptic(s) with force/displacement characteristics similar to or better than conventional loop haptics.

A preferred hydrogel for the haptic portion is a copolymer of one or more monomers of formula I, hydroxyethylmethacrylate and methylmethacrylate. The percentage of hydroxyethylmethacrylate is preferably less than about 50%, most preferably between about 25-50% hydroxyethylmethacrylate. The co-polymer used for the haptic portion generally has a lower water content in the hydrated form than the co-polymer used for the optic portion. In other co-polymers the combination of hydroxyethylmethacrylate and methylmethacrylate may be substituted by vinyl pyrrolidone and hydroxyethylmethacrylate or methyl methacrylate; glyceral methacrylate and methyl methacrylate; hydroxyethylmethacrylate/diacetone acyl amide and various other monomers such as hydroxyalkyl methacrylates and acrylates with the alkyl groups having from 2 to 6 carbon atoms; vinyl hydroxy acetate, vinyl hydroxy propionate, vinyl hydroxy butyrate; N-vinyl lactams namely N-vinyl pyrrolidone, N-vinyl caprolactam and N-vinyl piperidone; N,N-dialkyl amino ethyl methacrylates and acrylates with the alkyl groups having from 0 to 2 carbon atoms; hydroxyalkyl vinyl ethers with the alkyl groups having 2 to 4 carbon atoms; 1-vinyloxy 2-hydroxyethylene, 1-vinyloxy 5-hydroxy 3-oxapentane, 1-vinyloxy 8-hydroxy 3,6-dioxaoctane, 1-vinyloxy 14-hydroxy 3,6,9,12 tetraoxatetradectane; N-vinyl morpholine; N,N dialkyl acrylamide with the alkyl groups having from 0 to 2 carbons atoms; alkyl vinyl ketone with the alkyl group having 1 to 2 carbon atoms; N-vinyl succinimide and N-vinyl glutarimide; N-vinyl imidazole; and N-vinyl 3-morpholinone. It is noted that these preferred hydrogel co-polymers of the invention may not only be used in haptics of IOLs but also for the production of other articles of interest for which co-polymers are suited.

In another embodiment of the invention, co-polymers of the invention are prepared by co-polymerization of one or more compounds of formula I and one or more monomers of formula III:

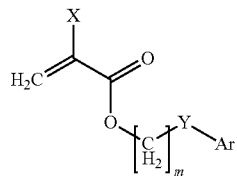

wherein: X is H or $CH_3$; m is 0-10; Y is nothing, O, S, or NR wherein R is H, $CH_3$, $C_nH_{2n+1}$ (n=1-10) iso-$OC_3H_7$, $C_6H_5$, or $CH_2C_6H_5$; Ar is any aromatic ring, such as benzene, which can be unsubstituted or substituted with H, $CH_3$, $C_2H_5$, n-$C_3H_7$, iso-$C_3H_7$, $OCH_3$, $C_6H_{11}$, Cl, Br, $C_6H_5$ or $CH_2C_6H_5$.

Suitable monomers of formula III include, but are not limited to: 2-ethylphenoxy methacrylate, 2-ethylphenoxy acrylate, 2-ethylthiophenyl methacrylate, 2-ethylthiophenyl acrylate, 2-ethylaminophenyl methacrylate, phenyl methacrylate, benzyl methacrylate, 2-phenylethyl methacrylate, 3-phenylpropyl methacrylate, 3-propylphenoxy methacrylate, 4-butylphenoxy metacrylate, 4-phenylbutyl methacrylate, 4-methylphenyl methacrylate, 4-methylbenzyl methacrylate, 2-2-methylphenylethyl methacrylate, 2-3-methylphenylethyl methacrylate, 2-4-methylphenylethyl methacrylate, 2-(4-propylphenyl)ethyl methacrylate, 2-(4-(1-methylethyl)phenyl)ethyl methacrylate, 2-(4-methoxyphenyl)ethylmethacrylate, 2-(4-cyclohexylphenyl)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates and acrylates.

The co-polymers of one or more compounds of formula I and one or more compounds of formula III are well suited for the manufacture of optical lenses with a high refractive index, in particular foldable IOLs. The co-polymers are prepared by generally conventional polymerization methods as described before. Suitable co-polymerizable cross-linking agents used in the co-polymers were also discussed before.

It will be understood by those skilled in the art, that among polymers of acrylic esters, those made from acrylate ester monomers tend to have lower glass transition temperatures and to be more flexible than polymers of methacrylate esters. Accordingly, the co-polymers used in foldable IOLs of this invention will generally comprise a greater mole percent of acrylate ester residues than of methacrylate ester residues. For co-polymers comprising monomers of formula III, it is preferred that the aryl acrylate monomers constitute from about 60 mole percent to about 95 mole percent of the polymer, while the aryl methacrylate monomers constitute from about 5 mole percent to about 40 mole percent of the polymer. Among co-polymers of the invention comprising one or more monomers of formula I and monomers of formula III, preferred co-polymers comprise about 10-20 mole percent of a monomer of formula I, 50-55 mole percent 2-phenylethyl acrylate and about 30-35 mole percent 2-phenylethyl methacrylate.

In a particular embodiment that relates to the production of soft, foldable IOL having high refractive indexes and soft contact lenses, one or more monomers of formula I are co-polymerized in the presence of a suitable cross-linking agent with two or three other monomers defined below, each of which monomers adds specific, desirable properties to the final polymer. The first such other monomer, which is preferably present in the co-polymers in an amount of at least about 10% or about 20% by weight and more preferably in a major amount (at least about 50%) by weight, is derived from a first monomeric component, the homopolymers of which have a refractive index of at least about 1.50, preferably at least about 1.52 or about 1.54. The homopolymers of the first monomeric component preferably have a substantial degree of rigidity. Particularly useful first monomeric components include styrene, vinyl carbazole, vinyl naphthalene, benzyl acrylate, phenyl acrylate, naphthyl acrylate, pentabromophenyl acrylate, 2-phenoxyethyl acrylate, 2-phenoxyethyl methacrylate, 2,3-dibromopropyl acrylate and mixtures thereof. The second other monomer is preferably present in an amount of at least about 2%, more preferably at least about 4% by weight of total monomers. Any suitable second monomeric component which meets the criteria for such component set forth herein may be employed. Homopolymers of the second monomeric component have glass transition temperatures of less than about 30° C., preferably less than about 22° C. Particularly useful second monomeric components include n-butyl acrylate, n-hexyl acrylate, 2-ethylhexyl acrylate, 2-ethoxyethyl acrylate, 2,3-dibromopropyl acrylate, n-1, 1-dihydroperfluorobutyl acrylate and mixtures thereof. The co-polymers may further include an additional hydrophilic monomeric component. The term "hydrophilic monomeric component" refers to compounds which produce hydrogel-forming homopolymers, that is homopolymers which become associated with substantial amounts, for example, at least about 20% based on the weight of the homopolymer, of water and which physically swell as a result of such association. Specific examples of useful hydrophilic monomeric components include N-vinyl pyrrolidone; hydroxyalkyl acrylates and hydroxyalkyl methacrylates, such as 2-hydroxyethyl acrylate, 2-hydroxyethyl methacrylate, 3-hydroxypropyl acrylate, 3-hydroxypropyl methacrylate, 4-hydroxybutyl acrylate, 4-hydroxybutyl methacrylate, 2,3-dihydroxypropyl acrylate, 2,3-dihydroxypropyl methacrylate and the like; acrylamide; N-alkyl acrylamides such as N-methyl acrylamide, N-ethyl acrylamide, N-propyl acrylamide, N-butyl acrylamide and the like; acrylic acid; methacrylic acid; and the like and mixtures thereof.

In another particular embodiment that is particularly useful for the production of soft, foldable IOL having high refractive indexes and soft contact lenses, co-polymers are made that comprise at least one monomer of formula I, at least one monomer of formula III, a suitable cross-linking agent and a hydrophilic monomer, the amount of which hydrophilic monomer is not greater than that of the aryl acrylic hydrophobic component of formula III. Suitable hydrophilic monomers include 2-hydroxyethyl acrylate; 2-hydroxyethyl methacrylate; 2-N-ethylacrylate pyrrolidone; 2-hydroxy-3-phenoxypropyl acrylate; 2,3-dihydroxypropyl acrylate; 2,3-dihydroxypropyl methacrylate; 2-N-vinyl pyrrolidone; polyethylene oxide:200 monomethyl ether monomethacrylate; polyethylene oxide:200 monomethacrylate; polyethylene oxide:1000 dimethacrylate. Preferred hydrophilic monomers for use in the present invention are include 2-hydroxyethyl acrylate; 2-hydroxyethyl methacrylate; and polyethylene oxide:1000 dimethacrylate.

An ultraviolet light-absorbing material can also be included in the co-polymers of the invention. This is of particular importance in the case of IOLs made from co-polymers of the invention, in which case inclusion of ultraviolet-absorbing material is intended to produce an absorbance approximately that of the natural lens of the eye. The ultraviolet-absorbing material can be any compound that absorbs ultraviolet light, i.e., light having a wavelength shorter than about 400 nm, but does not absorb any substantial amount of visible light. The ultraviolet-absorbing compound is incorporated into the monomer mixture and is entrapped in the polymer matrix when the monomer mixture is polymerized. Suitable ultraviolet-absorbing compounds include substituted benzophenones, such as 2-hydroxybenzophenone, and 2-(2-hydroxyphenyl) benzotriazoles. It is preferred to use an ultraviolet-absorbing compound that is co-polymerizable with the monomers and is thereby covalently bound to the polymer matrix. In this way possible leaching of the ultraviolet-absorbing compound out of an article made from co-polymers of the invention, e.g. from a lens into the interior of the eye, is minimized. Suitable co-polymerizable ultraviolet-absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. The most preferred ultraviolet absorbing compound is 2-(3'-methallyl-2'-hydroxy-5'methyl phenyl)benzotriazole. UV absorbers are typically present in an amount of 0.1-5 wt % of total monomers present.

It is also known that high-energy blue light can damage the retina. In fact, the human IOL produces yellow pigment that mitigates against such damage. Therefore, a blue light-absorbing compound may be included in the co-polymers of the invention when they are used to prepare IOLs. Suitable co-polymerizable blue light-blocking chromophores are described, e.g., in U.S. Pat. Nos. 4,528,311 and 5,470,932. Blue light absorbers are typically present in an amount of 0.01-0.5 wt % of total monomers present.

IOLs prepared using the co-polymers of the invention can have any suitable shape and size. Preferably, the optic portion of an IOL does not contain a tumble-polished edge but a square edge around the entire circumference including the junction with the haptics. Vargas et al. 2002. J Cataract Refract Surg 28, 1241-50.

Co-polymers of the invention can be shaped into drug delivery devices, whereby a drug is present in the matrix of the co-polymer. Such devices include implants, patches, lenses and the like. Contact lenses and IOLs made from co-polymers of the invention can be used as ophthalmic drug delivery devices for topically or systemically active drugs. Many different processes may be used for preparing such drug delivery devices that are capable of releasing an incorporated drug or medicament upon contact with tissue. The drug may be included in the monomer mixture to prepare a homogenous co-polymer containing a uniform distribution of drug. Alternatively, it may be possible to prepare sandwich-type delivery devices in which a drug is exclusively present in the middle layer but not in the outer layers. Yet another device may consist of two layers, of which only one contains drug. Drug may also be soaked into a co-polymer of the invention, i.e., introduced subsequent to polymerization. Illustrative examples of this preferred method for preparing a drug delivery device using co-polymers of the invention are presented in the example section.

In general, a therapeutically effective amount of a drug is an amount that produces a desired therapeutic effect for the intended period of time. The amount of drug that needs to be introduced into a drug-delivery device prepared from a co-polymer of the invention to produce a desired therapeutic effect of an appropriate duration depends on several known factors such as the physicochemical properties of the drug, the therapeutic efficacy of the drug and therapeutic effect to be achieved. It further will depend on the intended site of action of the drug, e.g., in the case of a lens whether systemic delivery is to be achieved or whether the therapeutic target is the cornea, conjunctiva, retina, lacrimal glands, etc. Typically, a drug may by present in a drug-containing layer of a co-polymer of the invention in an amount between about 0.1 wt % and about 15 wt % of total monomers present. The rate of drug release will vary with the degree of cross-linking, the polymeric composition, the type of barrier system used and the mode of drug loading. A person skilled in the art will know how to vary these factors to achieve a desired result with only minimal experimentation. Before a drug delivery device is tested on an experimental animal, the characteristics of drug release can be tested in vitro. For example, to test release from a pilacarpine-containing lens, lenses with and without drug can be placed in a known quantity of release media (distilled water or buffered saline) and stirred with a magnetic stirrer. At various times the lenses can be transferred to fresh media and the absorbance of the previous media can be determined by ultraviolet spectroscopy. The absorbance of the media containing drugged lenses is reduced by the absorbance of the media containing undrugged lenses. Use of a calibration curve relating absorbance to concentration allows for a determination of the concentration of the drug. The calibration curve is developed by measuring the absorbance of known concentrations of the drug in the release media. As the concentrations (microgram/ml) of the drug and the volume (ml) of release media are known, the amount of the released drug can be calculated (microgram). This value divided by the time of exposure to the media gives the release rate in microgram/hr that is plotted against time.

Examples of drugs that may be delivered using delivery devices made of co-polymers of the invention such as implants, transdermal patches, contact lenses and the like include, but are not limited to, antibiotics, antivirals, steroidal and nonsteroidal anti-inflammatories, steroids, peptides, polypeptides, cardiotonics, antihypertensives, antiallergics, alpha- and beta-adrenergic blocking agents, pain managers, and anti-cancer agents. Ophthalmic medicaments delivered by means of a drug-loaded contact lens comprise anti-infectives, including, without limitation, antibiotics, antivirals, and antifungals; antiallergenic agents and mast cell stabilizers; steroidal and non-steroidal anti-inflammatory agents; combinations of anti-infective and anti-inflammatory agents; decongestants; anti-glaucoma agents, including, without limitation, adrenergics, .beta-adrenergic blocking agents, .alpha-adrenergic agonists, parasypathomimetic agents, cholinesterase inhibitors, carbonic anhydrase inhibitors, and prostaglandins; combinations of anti-glaucoma agents; antioxidants; nutritional supplements; drugs for the treatment of cystoid macular edema including, without limitation, non-steroidal anti-inflammatory agents; drugs for the treatment of ARMD, including, without limitation, angiogenesis inhibitors and nutritional supplements; drugs for the treatment of herpetic infections and CMV ocular infections; drugs for the treatment of proliferative vitreoretinopathy including, without limitation, antimetabolites and fibrinolytics; wound modulating agents, including, without limitation, growth factors; antimetabolites; neuroprotective drugs, including, without limitation, eliprodil; and angiostatic steroids for the treatment of diseases or conditions of the posterior segment of the eye, including, without limitation, ARMD, CNV, retinopathies, retinitis, uveitis, macular edema, and glaucoma. Such angiostatic steroids are more fully disclosed in U.S. Pat. Nos. 5,679,666 and 5,770,592, which are incorporated herein in their entirety by reference. Preferred ones of such angiostatic steroids include 4,9(11)-Pregnadien-17-alpha, 21-diol-3,20-dione and 4,9(11)-Pregnadien-17-alpha, 21-diol-3,20-dione-21-acetate. Specific compounds encompass, without limitation, pilocarpine, idoxuridine, carbachol, bethanechol, timolol, tetracycline, epinephrine, phenylephrine, eserine, phospholine, demecarium, cyclopentolate, homatropine, scopolamine, nitroglycerin, chlortetracycline, bacitracin, neomycin, polymyxin, gramicidin, oxytetracycline, chloramphenicol, gentamycin, penicillin, erythromycin, sulfacetamide, polymyxin B, tobramycin, isofluorophate, fluoromethalone, dexamethasone, hydrocortisone, fluorocinolone, medrysone, prednisolone, methyl prednisolone, betamethasone, triamcinolone, interferon, cromolyn, all-trans-retinoic acid (Vitamin A), and the nontoxic, pharmaceutically acceptable salts thereof and the like. Drugs such as Apraclonidine, Anecortave acetate, Lodoxamide, Olopatadine hydrochloride and Cyclosporine A are also specifically included. The category of ophthalmic lubricating agents refers to those agents capable of inducing natural lacrimation or creating artificial lacrimation and includes, for example, polyvinyl alcohol, cellulose polymers such as hydroxypropyl methyl cellulose, a polylactam such as polyvinyl pyrrolidinone and other tear inducers or substitutes. The topical or regional anesthetic agents, which may be useful during ophthalmic surgery or other ophthalmic procedures, include lidocaine, cocaine, benoxinate, dibucaine, proparacaine, tetracaine, etidocaine, procaine, hexylcaine, bupivacaine, mepivacaine, prilocaine, chloroprocaine, etc.

The term "pharmaceutically acceptable salt" refers to those salts of the parent compound that do not significantly or adversely affect the pharmaceutical properties (e.g., toxicity, efficacy, etc.) of the parent compound. Pharmaceutically acceptable salts of the present invention include, for example, chloride, iodide, bromide, hydrochloride, acetate, nitrate, stearate, phosphate, sulfate etc.

An IOL, when surgically implanted, is typically designed to replace a previously or simultaneously removed cataractous lens. Cataract surgery including implantation of the IOL may result in inflammatory responses. To minimize these responses, an IOL made from a co-polymer of the invention may include an appropriate amount of an anti-inflammatory drug such as, for example, indomethacin, diclofenac, dexamethasone, or triamcinolone. Additional drugs may be included to prevent late secondary fibrosis and/or neovascularization.

Polymers of side chain-active acrylic amino acids can be used as filling materials for breast implants. The polymers may also be employed for the manufacture of ointments of any kind, food and cosmetic additives, additives for patches, space fillers for surgery, and the like.

Co-polymers comprising side chain-active acrylic amino acids and other types of monomers as described herein may not only be used for manufacturing optical lenses such as contact lenses or IOLs but also for preparing many other products characterized as products that come in contact with skin, tissue or body fluid. The products include all implants, blood processing devices such as hemodialyzers, oxygenators, membrane plasmapheresis modules, dentures, crowns, dental fillings, catheters, tubing, wound and burn dressings, and the like. They also include barrier devices (e.g., condoms, gloves, face shields, etc.), diapers, tampons, blood bags and tubings, test tubes, syringes, wound healing slabs, coatings and beads for cell cultures, conductive plastics and articles of clothing (fibers).

In particular, co-polymers of the invention are suitable for the preparation of heart pacemakers, tachyarrhythmia controllers, heart valves, vascular grafts, breast implants, disc fillers in cosmetic and reconstructive surgery, orthopedic implants, synthetic bone grafts, joint lubrication, dental implants, crowns and bridges, dental fillers and cements, penile and testicular implants, injectables for urinary incontinence, hydrocephalus shunts, drug delivery implants, blood oxygenators (membrane oxygenators), intravascular oxygenators, hemoconcentrators, catheters for stenosis, IV and CVC catheters, heart assist devices such as intraaoritc balloon pump and ventricular assist devices, dentures and denture adhesives, dental impression materials, artificial kidneys, balloon catheters for renal, urological and gastroenterological applications, sample collection and processing, transdermal drug delivery devices such as TDD patches, wound care closures and dressings, sutures and staples.

The invention is further illustrated by the following examples that are intended to be illustrative, but not limiting.

EXAMPLES

Example 1

Synthesis of Acryl Lysine Monomers Via Copper Complex 14.62 g (0.1 moles) L-lysine (Fluka 62840) was dissolved in 150 ml deionized water and heated to about 80° C. 16.6 g (0.075 moles) copper carbonate (Fluka 61167) were added in portions during about 30 minutes. The reaction mixture was subsequently heated in a closed system and stirred during about 30 minutes. The hot, deep-blue suspension was filtered through silicagel. The filter was washed with a small amount of water. On the subsequent day, the lysine-copper complex-containing filtrate was cooled in an icebath, and 100 ml tetrahydrofuran were added. Acryl chloride (8.9 ml; 0.11 moles; Fluka 01780) was added dropwise during a period of about an hour. The pH was initially maintained between 8 and 10 by parallel, dropwise addition of 10% sodium hydroxide. After about half of the acryl chloride solution had been added, product began to precipitate. As most of the acryl chloride had been added, base addition was slowed to allow the pH to drop to about 6 and the temperature of the reaction mixture to reach room temperature. The blue suspension was stirred during an additional 2 hours and was then filtered. The solid material retained by the filter was washed with water and acetone and then dried. A yield of 6.5 g of acryllysine copper complex was observed.

29.5 g of acryllysine copper complex were suspended in 300 ml deionized water and cooled in an ice bath. $H_2S$ was bubbled into the suspension until copper sulfide precipitation was complete. 3 g active charcoal was added to the suspension. The suspension was heated shortly to 100° C. After cooling to room temperature, 500 ml acetone were added to the suspension which was then filtered over silicagel. The clear filtrate was put in a rotary evaporator. After evaporation of the solvent, the solid product was recrystallized from 200 ml 50% aqueous acetone. A yield of 17.76 g (69.76%) of white powder was observed. The structure of the compound was identified by NMR and LC-MS spectroscopy.

Example 2

Synthesis of Acryl Serine, Acryl Threonine, Acryl Tyrosine, Acryl Oxiproline and Acryl Cysteine Synthesis of these compounds was performed as described in Example 1. For acryl cysteine, the starting material was cystine.

Example 3

Synthesis of Fmoc-Acryl-Lysine 10 g of acryl-lysine were dissolved in 106 ml of a 10% (wt/vol) solution of sodium carbonate in water and diluted with 100 ml dioxane. 14 g Fmoc-chloride dissolved in 50 ml dioxane were added to the reaction mixture over a period of 30 minutes at 15-25° C. The reaction mixture was stirred for 3 h at room temperature and then adjusted to pH2 with the addition of 10% aqueous HCl. After extraction with ethyl acetate, the organic phase was evaporated to dryness. 21.4 g of the resulting clear yellowish oil were put on 200 g silicagel and washed with ethyl acetate. The product was extracted from the silicagel with 3:1 (vol/vol) ethyl acetate/methanol. After evaporation of the solvent, a white powder (10.4 g equal to a 50% yield) was obtained. The structure of the compound was verified by NMR.

Example 4

Synthesis of Fmoc-Acryl Serine, Fmoc-Acryl Threonine, Fmoc-Acryl Tyrosine, Fmoc-Acryl Oxiproline and Fmoc-Cysteine Synthesis of these compounds was performed as described in Example 3.

Example 5

Synthesis of Methacryl Derivatives of Alpha-Amino-Protected and Unprotected Amino Acids Synthesis of methacryl-derivatives was performed using methacryl chloride under conditions described in Examples 1 through 4.

Example 6

Biocompatibility of Co-Polymers of the Invention and Prior Art Polymers

The non-biodegradable polymers and co-polymers of the invention have a surprisingly high biocompatibility (or biophilicity). This was evident from a comparative analysis of proliferation of primary fibroblasts from human embryonic tissue on slabs of the different polymers listed in Table 1.

TABLE 1

Comparison of biocompatibilities of state of the art polymers and co-polymers of the invention

| Characterization of Polymer | Monomers for polymerization | Ratio (wt % of monomers) | Percent Confluence |
|---|---|---|---|
| Control (Collagen, a natural protein) | — | — | 100 |
| State of the Art Polymers | MMA | 100 | 9 |
| | HEMA | 100 | 13 |
| | AA/HEMA | 90/10 | 18 |
| | ACN | 100 | 5 |
| | PEA/PEMA | 60/40 | 10 |
| U.S. Pat. No. 4,668,506 | HEMA/IBOMA/MG | 80/10/5 | 12 |
| | HEMA/GMA | 85/15 | 8 |
| Biopolymers of the Invention | ACN/LMA | 95/5 | 65 |
| | HEMA/AA/SA | 10/80/10 | 69 |
| | HEMA/LA | 90/10 | 95 |
| | HEMA/SA | 85/15 | 91 |
| | HEMA/SMA | 90/10 | 96 |
| | HEMA/TA | 90/10 | 89 |
| | MMA/LA | 80/20 | 84 |
| | MMA/LMA | 80/20 | 81 |
| | MMA/SMA | 80/20 | 77 |
| | PEA/PEMA/CMA | 60/25/10 | 95 |
| | PEA/PEMA/LA | 60/30/5 | 92 |
| | PEA/PEMA/TA | 60/25/10 | 87 |
| | PEA/PEMA/TMA | 60/25/10 | 89 |

ACN: acrylnitrile; LMA: Fmoc-lysinyl-methacrylate; HEMA: 2-hydroxyethyl-methacrylate; AA: acrylamide; SA: Fmoc-serinyl-acrylate; LA: Fmoc-lysinyl-acrylate; SMA: Fmoc-serinyl-methacrylate; TA: Fmoc-tyrosinyl-acrylate; MMA: methylmethacrylate; PEA: 2-phenylethyl-acrylate; PEMA: 2-phenylethyl-methacrylate; CMA: Fmoc-cysteinyl-methacrylate; TMA: Fmoc-tyrosinyl-methacrylate; IBOMA: isobornylmethacrylate; MG: methacrylglycine; GMA glycerylmethacrylate.

Circular polymer slabs for insertion in polycarbonate petri dishes (2 cm in diameter) were prepared as follows. Pairs of 5-cm rectangular glass plates separated by 2-mm spacers were filled with ultrapure (>99.9%) monomers or monomer mixtures in the ratios listed in Table 1. All compositions contained 0.5 wt % ethyleneglycol dimethacrylate and 0.5 wt % azobisisobutyronitrile. For polymerization the filled and sealed glass chambers were heated at 40° C. for 5 hours and post-cured at 90° C. for 6 hours. The polymerized slabs were removed from the glass plates, incubated in 100 ml dimethylformamide/piperidine (80 wt %/20 wt %) for 6 hours at room temperature to effect Fmoc-deprotection, rinsed 3 times with 50 ml dimethlyformamide for 3 hours and finally incubated 3 times with 100 ml phosphate buffered saline (50 mM sodium phosphate, 0.8% NaCl, pH 7.2). Circular slabs (1.9 cm in diameter) were cut from the rectangular slabs and were placed into 2-cm petri dishes. The dishes were autoclaved for 20 minutes at 120° C. To the sterile dishes were added 2 ml of Dulbecco's modified Eagle medium buffered with 2.2 g/l sodium bicarbonate and supplemented with 5% fetal calf serum, 10% heat-inactivated horse serum, 100 U/ml penicillin and 100 µg/ml streptomycin. After being seeded with primary fibroblasts from human embryonic tissue (obtained from the hospital of the University of Basel, Switzerland) to 5% confluency, the dishes were incubated at 37° C. and under 5% $CO_2$. Medium was changed every 24 hours. Collagen coating of petri dishes was performed by adding 2 ml of a 10 wt % aqueous solution of porcine collagen to petri dishes and incubating the dishes for 30 minutes at room temperature. Percentage confluency was determined from an analysis of photographs of different cultures taken at the end of the experimental period.

Example 7

Biopolymers for Breast Implants

A mixture of 10 wt % lysinyl-acrylate, 10 wt % serinyl-acrylate and 0.5 wt % azo-bis-isobutyronitrile initiator in 79.5 wt % degassed water was prepared. Polymerization occurred at 60° C. for 7 days. Thereafter 5 parts of isopropanol were added to one part of polymerization mixture, and precipitated polymer was isolated. Polymer was dissolved in saline (1:5 wt/wt). The resulting gel can be used for filling bags used for breast implants. The same type of pure, amino acid-based biopolymer can be used for the manufacture of thickeners for food, cosmetics and drug ointments, food additives, additives for patches and space fillers for plastic surgery.

Example 8

Production of Artificial Discs and Replacement Vessels Using a Lysineamidyl Methacrylate-Containing Copolymer A mixture of 80 wt % methylmethacrylate, 19 wt % Fmoc-L-lysineamidyl methacrylate, 0.5 wt % ethylene glycol diacrylate and 0.5 wt % azobisisobutyronitrile was poured into polypropylene molds for artificial discs or artificial vessels (tubes). To achieve polymerization, the molds were heated gradually from 20° C. to 100° C. over a period of 24 hours. For deprotection, the polymer was treated as described in Example 6. The water content in the mixed polymer was 80 wt % as determined from the weight increase after soaking in phosphate buffered saline. The composition of the polymer mixture was determined quantitatively by staining amino acid residues using the ninhydrine method. The result indicated that 18 wt %±2 wt % L-lysineamidyl-methacrylate had copolymerized with methylmethacrylate.

Example 9

Production of Artificial Discs and Replacement Vessels Using a Serinyl Methacrylate-Containing Copolymer The procedure of Example 8 was followed, except that Fmoc-L-lysineamidyl-methacrylate was substituted with Fmoc-L-serinyl-methacrylate.

Example 10

Wound-Healing Slabs for Third Degree Skin Burns

A mixture of 5 wt % acrylamide, 3 wt % 2-hydroxyethylmethacrylate, 2 wt % L-serinyl acrylate and 0.5 wt % ethylenediamine-bisacrylamide were dissolved in water and polymerized with 0.01 wt % sodium peroxodisulfate in polypropylene molds for obtaining 5×10×0.3 cm slabs. If required, the resulting slabs can be loaded with drugs (wound healing accelerators, antiinfectives, pain managers, antiinflammatories or combinations thereof) as described in Example 23.

Example 11

Spinnable Fibers for Surgical Threads and Fabrics

A mixture of 94 wt % acrylonitrile (ACN), 5 wt % Fmoc-L-lysinyl-methacrylate and 1 wt % 2,4,6 trimethyl-benzoyldiphenylphosphine-oxide was copolymerized using blue light as initiator of polymerization. Deprotection was effected as described in Example 6. After dilution of the dimethylformamide-containing reaction mixture with 10 parts of water, the precipitated polymer can be dried and readily used for spinning fibers. Such fibers will take on water up to an amount corresponding to 20 wt % of dry polymer, resulting in wool- or silk-like fabrics with humidity exchange properties that depend on the weaving process used.

Examples 12-17 relate to the manufacture of intraocular lenses (IOLs).

Example 12

A bicomposite IOL consisting of an optic made from a co-polymer of 2-hydroxyethylmethacrylate and L-lysineamidyl acrylate and a haptic made from a copolymer of 2-hydroxyethylmethacrylate, L-lysineamidyl acrylate and methylmethacrylate was manufactured by the following procedure:

45 wt % 2-hydroxyethylmethacrylate, 45 wt % methylmethacrylate, 9 wt % Fmoc L-lysineamidyl acrylate; 0.5 wt % ethylene glycol dimethacrylate and 0.5 wt % azobisisobutyronitrile were mixed and poured into sealed 15×15 mm injection-molded polypropylene cylindrical molds. The molds were heated gradually from 20° C. to 100° C. over a period of 48 hours. The resulting co-polymer was removed from the molds, and a 6-mm hole was drilled into each polymer cylinder to a depth of 13 mm. The cylinders were put back into the molds, and a mixture of 90 wt % 2-hydroxyethylmethacrylate, 9 wt % Fmoc-L-lysineamidyl acrylate, 0.5 wt % ethylene glycol dimethacrylate and 0.5 wt % azobisisobutyronitrile was filled into the holes, and the molds were heated gradually to 80° C. over a period of 36 hours.

The cylinders were removed from the molds and the tops, bottoms and edges lathed to form 1 mm-thick bottoms. The IOLs were treated for deprotection as described in Example 6, producing a lens with a soft flexible optic and a rigid but still hydrophilic haptic.

Example 13

The procedure for producing IOLs described in Example 12 was followed, except that Fmoc-L-serinyl methacrylate was used instead of Fmoc-L-lysineamidyl acrylate.

Example 14

The procedure for producing IOLs described in Example 12 was followed, except that Fmoc-L-threoninyl acrylate was used instead of Fmoc-L-lysineamidyl acrylate.

Example 15

A copolymer was manufactured by mixing 60 wt % 2-phenylethylacrylate, 25 wt % 2-phenylethylmethacrylate, 10 wt % Fmoc-tyrosinyl methacrylate, 3.5 wt % 1,4-butanediol diacrylate, 1.5 wt % 2-(3'-methallyl-2'-hydroxy-5'-methyl phenyl)benzotriazole and 1.7 wt % thermal initiator di-(tert-butylcyclohexyl) peroxydicarbonate. The mixture was poured into sealed polypropylene molds in the shape of IOLs and heated gradually to 100° C. over a period of 12 hours. The IOLs were treated for deprotection as described in Example 6.

Example 16

The procedure of Example 15 was followed, except that Fmoc-tyrosinyl methacrylate was replaced by Fmoc-tyrosyl acrylate.

Example 17

The procedure of Example 15 was followed, except that Fmoc-tyrosinyl methacrylate was replaced by Fmoc-cysteinyl methacrylate.

Examples 18 and 19 relate to the manufacture of contact lenses.

Example 18

Hard Contact Lenses

A mixture of 80 wt % methylmethacrylate, 19 wt % Fmoc-L-lysineamidyl acrylate, 0.5 wt % ethylene glycol diacrylate and 0.5 wt % azobisisobutyronitrile was polymerized in molds for contact lens production under gradual heating as described in previous examples. After deprotection and equilibration again phosphate buffered saline, the hard contact lenses contained 75-80% water.

Example 19

Soft Contact Lenses 85 wt % 2-hydroxyethylmethacrylate, 14 wt % Fmoc-serinyl acrylate (SA), 0.5 wt % ethylene glycol diacrylate and 0.5 wt % azobisisobutyronitrile were polymerized in molds for contact lens production under gradual heating as described in previous examples. Deprotection and equilibration again phosphate buffered saline was as in example 18.

Examples 20 and 21 relate to the manufacture of topical, transdermal, and transcorneal and systemic drug delivery systems (ocular drug delivery systems or ODDS) and to methods of loading these devices with drug substances. Generally useful drugs for delivery using ODDS include anti-glaucoma drugs, e.g. β-blockers, carbonic anhydrase inhibitors, prostaglandins, nonsteroidal and steroidal anti-inflammatory drugs, anesthetics, pain managers, anti-cancer agents, lacrimation inducers and anti-infective drugs.

Example 20

ODDS for Hydrophobic Drugs

A copolymer was manufactured by mixing 60 wt % 2-phenylethylacrylate, 30 wt % 2-phenylethylmethacrylate, 5 wt % Fmoc-L-lysineamidyl acrylate, 3.5 wt % 1,4-butanedioldiacrylate and 1.5 wt % thermal initiator di-(tert-butylcylohexyl)peroxy dicarbonate. The mixture was polymerized in polypropylene molds for ODDS production (optical or non optical) as described in Example 15.

Example 21

ODDS for Hydrophilic Drugs 80 wt % 2-hydroxyethylmethacrylate, 19 wt % Fmoc-L-lysineamidyl acrylate, 0.5 wt % ethylene glycol diacrylate and 0.5 wt % azobisisobutyronitrile were polymerized in molds for ODDS (optical or non optical) production as described in Example 12.

Example 22

Loading of an ODDS with Hydrophobic Drugs, e.g., for the Treatment of Age-Related Macular Degeneration (AMD) or Post Cataract Surgery Inflammation The ODDS (optical or non optical) described in Example 20 was immersed for 8 hours at room temperature in dimethyl formamide containing 5 mg/ml Triamcinolone. Thereafter, the lens was equilibrated in saline solution for 24 hours. Each lens contained 0.5 mg of the drug. Instead of Triamcinolone, Anecortave Acetate or other hydrophobic steroids can be incorporated in lenses using the same drug-loading procedure.

Example 23

Loading of an ODDS with Hydrophilic Drugs, e.g., for the Treatment of Ocular Inflammations Generally and of Inflammation Occurring Subsequent to Cataract Surgery The ODDS (optical or non optical) described in Example 21 was immersed for 8 hours at room temperature in dimethyl formamide containing 20 mg/ml dexamethasone. Thereafter, the lens was equilibrated in saline solution containing 20 mg/ml dexamethasone for 24 hours. Each lens contained 2 mg of the drug.

The IOLs described in Examples 12 through 17 can also serve as ODDS and be loaded with a drug according to the procedures described in Examples 22 and 23. For example, an IOL prepared as explained in Examples 12 through 17 can be loaded with a steroidal or non-steroidal anti-inflam-

The invention claimed is:

1. Devices selected from the group consisting of, blood processing devices, intravascular oxygenators, dental implants, dental fillers, artificial bones, catheters, tubing, wound care closures and wound dressings, sutures and staples, condoms, face shields, diapers, tampons, coating and beads for cell cultures, heart pacemakers, tachyarrhythmia controllers, heart valves, vascular grafts, breast implants, fillers in cosmetic and reconstructive surgery, orthopedic implants, synthetic bone grafts, penile and testicular implants, hydrocephalus shunts, patches for transdermal drug delivery, conductive plastics and articles for clothing, the devices made from a co-polymer comprising (i) one or more polymerizable principal monomers, the principal monomers selected from the group consisting of an alkyl ester of acrylate or methacrylate, a hydroxyalkyl ester of acrylate or methacrylate, an N-alkyl acrylamide, acrylonitrile and a monomer of the formula

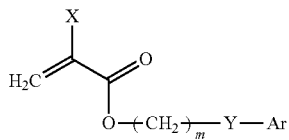

wherein:

X is H or $CH_3$; m is 0-10; Y is nothing, O, S, or NR wherein R is H, $CH_3$, $C_nH_{2n+1}$ (n=1-10) iso-$OC_3H_7$, $C_6H_5$, or $CH_2C_6H_5$; Ar is any aromatic ring, which can be unsubstituted or substituted with H, $CH_3$, $C_2H_5$, iso-$C_3H_7$, $OCH_3$, $C_6H_{11}$, Cl, Br, $C_6H_5$ or $CH_2C_6H_5$;

(ii) one or more co-principal monomers of the formula

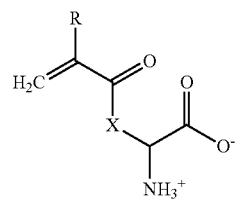

wherein:

X is —$NH(CH_2)_4$—, —O—$C_6H_4$—$CH_2$—, —O—CH($CH_3$)— or —S—$CH_2$—, R is H or $CH_3$; and the co-principal monomers and the principal monomers are present at a weight ratio between 1:99 and 1:1;

(iii) a free radical initiator and (iv) optionally, a cross-linking agent having a plurality of polymerizable ethylenically unsaturated groups.

2. The devices of claim 1 wherein X is —$NH(CH_2)_4$.

3. The devices of claim 1 wherein X is —O—$C_6H_4$—$CH_2$—.

4. The devices of claim 1 wherein X is —O—CH($CH_3$)—.

5. The devices of claim 1 wherein X is —S—$CH_2$—.

6. The devices of claim 1 wherein co-principal and principal monomers are present at weight ratios of between about 1:19 and 1:4.

7. A device according to claim 1, wherein the device further comprises a therapeutically effective amount of a drug.

8. The device of claim 7 wherein X is —$NH(CH_2)_4$.

9. The device of claim 7 wherein X is —O—$C_6H_4$—$CH_2$—.

10. The device of claim 7 wherein X is —O—CH($CH_3$)—.

11. The device of claim 7 wherein X is —S—$CH_2$—.

12. The device of claim 7 wherein co-principal and principal monomers are present at weight ratios of between about 1:19 and 1:4.

* * * * *

UNITED STATES PATENT AND TRADEMARK OFFICE
CERTIFICATE OF CORRECTION

PATENT NO. : 9,839,719 B2  Page 1 of 1
APPLICATION NO. : 11/920507
DATED : December 12, 2017
INVENTOR(S) : Hitz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1371 days.

Signed and Sealed this
Twenty-fifth Day of September, 2018

Andrei Iancu
*Director of the United States Patent and Trademark Office*